US005912371A

United States Patent [19]
Nakanishi et al.

[11] Patent Number: 5,912,371
[45] Date of Patent: Jun. 15, 1999

[54] METHOD FOR PREPARING FATTY ACID CHLORIDES

[75] Inventors: Koji Nakanishi, Kanagawa Prefecture; Tadashi Okawa, Chiba Prefecture, both of Japan

[73] Assignee: Dow Corning Toray Silicone Co., Ltd., Tokyo, Japan

[21] Appl. No.: 08/958,504

[22] Filed: Oct. 27, 1997

[30] Foreign Application Priority Data

Oct. 29, 1996 [JP] Japan .................................. 8-303738

[51] Int. Cl.[6] .................................................. C07C 51/363
[52] U.S. Cl. ........................ 554/159; 562/856; 562/857; 562/861; 556/465; 570/216; 570/217
[58] Field of Search ............................. 554/159; 562/866, 562/857, 861; 556/465; 570/216, 217

[56] References Cited

U.S. PATENT DOCUMENTS 4,072,710  2/1978  Coll ........................................ 260/544
4,163,108  7/1979  Beerthuis et al. ...................... 560/121

FOREIGN PATENT DOCUMENTS

A2-9837  of 1990  Japan .

*Primary Examiner*—Gary Geist
*Assistant Examiner*—Deborah D Carr
*Attorney, Agent, or Firm*—Patricia M. Scaduto

[57] ABSTRACT

A method for preparing fatty acid chlorides. The method comprises reacting a silylation product of a fatty acid comprising at least 2 aliphatically unsaturated bonds per molecule and a chlorinating agent.

20 Claims, No Drawings

METHOD FOR PREPARING FATTY ACID CHLORIDES

BACKGROUND OF THE INVENTION

1. Field of the Invention

This invention relates to a method for preparing fatty acid chlorides. More particularly, the invention relates to a method for preparing fatty acid chlorides comprising at least 2 aliphatically unsaturated bonds per molecule.

2. Background Information

Fatty acid chlorides are useful as reactive intermediates and are employed in a variety of organic synthetic reactions. While fatty acid chlorides can reportedly be synthesized by reacting a fatty acid with a chlorinating agent such as thionyl chloride, the reaction of a chlorinating agent with a fatty acid that contains 2 or more aliphatically unsaturated bonds per molecule produces side reactions that are thought to originate with the unsaturated bonds so that the desired fatty acid chloride is not obtained. Japanese Patent Application Laid Open (Kokai or Unexamined) Number Hei 2-9837 (9,837/1990) does teach a method for preparing acid chlorides of fatty acids that contain at least 2 aliphatically unsaturated bonds per molecule. In the method taught in this reference, the reaction is carried out by the addition of oxalyl chloride in small portions at a temperature of −15° C. to 5° C. to the aliphatically unsaturated fatty acid dissolved in a nonpolar solvent. While this method does inhibit the side reactions and provide the desired fatty acid chloride, it uses nonpolar solvent and requires that the reaction temperature be maintained in an extremely narrow and low temperature range. The reference method is therefore unsuitable for large-scale reactions and has poor productivity.

The inventors achieved the present invention as a result of extensive research directed to solving the problems described above. The objective of the present invention is to provide a method for preparing fatty acid chlorides comprising at least 2 aliphatically unsaturated bonds per molecule.

SUMMARY OF THE INVENTION

The present invention is a method for preparing fatty acid chlorides. The method comprises reacting a silylation product of a fatty acid comprising at least 2 aliphatically unsaturated bonds per molecule and a chlorinating agent.

DETAILED DESCRIPTION OF THE INVENTION

A method for preparing fatty acid chlorides comprising reacting (A) a silylation product of a fatty acid comprising at least 5 but no more than 30 carbon atoms and at least 2 aliphatically unsaturated bonds per molecule; and (B) a chlorinating agent.

Component (A) in the present invention is a silylation product resulting from the silylation of a fatty acid comprising at least 2 aliphatically unsaturated bonds per molecule. These compounds are synthesized by combining and reacting a silylating agent with a fatty acid comprising at least 2 aliphatically unsaturated bonds per molecule.

The fatty acid comprising at least 2 aliphatically unsaturated bonds per molecule is exemplified by higher fatty acids such as linoleic acid, eleostearic acid, hexadecatetraenoic acid, arachidonic acid and docosapentaenoic acid. Additional examples are drying oil fatty acids, e.g., soy oil fatty acid, tung oil fatty acid and dehydrated castor oil fatty acid. Among the preceding, drying oil fatty acids, which are mixtures of the above-mentioned higher fatty acids, are preferred for their ease of acquisition and cost effectiveness.

The silylating agent is exemplified by trimethylchlorosilane, tert-butyldimethylchlorosilane, triisopropylchlorosilane, hexamethyldisilazane and n-trimethylsilylimidazole.

The chlorinating agent (B) used in the present invention is exemplified by phosphoryl chloride, thionyl chloride, phosphorus pentachloride and phosphorus trichloride.

The above-described components (A) and (B) are reacted in the present invention. The ratio of moles of component (A) to moles of component (B) preferably falls within the range from 1:1 to 1:1.5. Although this reaction can proceed at temperatures above −30° C., it is generally carried out at temperatures in the range from −10° C. to 50° C.

This reaction runs according to the following equation when thionyl chloride is used as component (B).

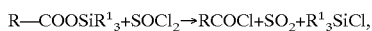

$$R\text{—}COOSiR^1{}_3 + SOCl_2 \rightarrow RCOCl + SO_2 + R^1{}_3SiCl,$$

where R is a monovalent hydrocarbon group comprising at least 2 aliphatically unsaturated bonds; and $R^1$ is an alkyl group. The sulfur dioxide ($SO_2$) and trialkylchlorosilane ($R^1{}_3SiCl$) reaction by-products also generated by this reaction can be easily distilled off under reduced pressure to yield the desired acid chloride (ROOCl) as a pure product.

Components (A) and (B) can be reacted neat in the present invention, but they can also be reacted in organic solvent. Useful organic solvents are exemplified by n-hexane, n-heptane, toluene, and the like. The reaction by-products generated during this reaction can be easily distilled off under reduced pressure to give the desired fatty acid chloride as a pure product.

The fatty acid chlorides comprising at least 2 aliphatically unsaturated bones per molecule that are synthesized by the present method are useful as reactive intermediates for the synthesis of amide and ester compounds. The reactivity of amides and esters comprising at least 2 aliphatically unsaturated bonds permits the utilization of such amides and esters as modifiers, improvers, surface-treatment agents, crosslinkers, and the like for various resins.

EXAMPLES

The invention is explained below in greater detail through examples.

Reference Example 1

Synthesis of Silylated Dehydrated Castor Oil Fatty Acid

Operating under nitrogen, 50 g dehydrated castor oil fatty acid (mixed fatty acid composed of 60% conjugated linoleic acid, 30% nonconjugated linoleic acid, 7% oleic acid, 2% stearic acid, and 1% palmitic acid), 50 ml toluene, and 20 ml pyridine were stirred in flask. 29 ml trimethylsilyl chloride was then added dropwise and the reaction was stirred for 1.5 hours. The precipitate was subsequently filtered. The low boilers were distilled from the filtrate under reduced pressure to give 57 g silylated dehydrated castor oil fatty acid.

Example 1

Synthesis of Dehydrated Castor Oil Fatty Acid Chloride

Operating under nitrogen, 56 g of the silylated dehydrated caster oil fatty acid prepared in Reference Example 1 was introduced into a flask and stirred. 18.8 g thionyl chloride was then added dropwise at room temperature. After stirring one hour, the by-products were distilled off from the reaction solution under reduced pressure to give 54 g dehydrated castor oil fatty acid chloride. This dehydrated castor oil fatty acid chloride was analyzed by $^{13}$C-NMR. The $^{13}$C-NMR chart showed that the pattern for the double-bonded carbon was almost unchanged from that of the precursor fatty acid, which indicated that the double bonds remained in their original state.

Comparative Example 1

Operating under nitrogen, 15 g dehydrated castor oil fatty acid was introduced into a flask and stirred. 7.0 g thionyl chloride was they added dropwise at room temperature. After stirring for 4 hours, the by-products were distilled out from the reaction solution under reduced pressure to give 17 g dehydrated castor oil fatty acid chloride. The pattern for the double-bonded carbon in the $^{13}$C-NMR chart was substantially altered from that for the precursor fatty acid. Moreover, its smaller integration value also indicated that side reactions had occurred in the double-bonded region. The $^{1}$H-NMR chart also gave a reduced integration value for the double bonding.

We claim:

1. A method for preparing fatty acid chlorides comprising reacting
   (A) a silylation product of a fatty acid comprising at least 5 but no more than 30 carbon atoms and at least 2 aliphatically unsaturated bonds per molecule; and
   (B) a chlorinating agent.
2. The method of claim 1 where the fatty acid is selected from the group consisting of a higher fatty acid and a drying oil fatty acid.
3. The method of claim 1 where the silylation product of a fatty acid is the silylation product of a drying oil fatty acid.
4. The method of claim 3 where the drying oil fatty acid is selected from the group consisting of soy oil fatty acid, tung oil fatty acid and dehydrated castor oil fatty acid.
5. The method of claim 3 where the silylation product of the drying oil fatty acid is a silylation product of a dehydrated castor oil fatty acid.
6. The method of claim 3 where the reaction is carried out at temperatures above −30° C.
7. The method of claim 5 where the reaction is carried out at temperatures in the range from −10° C. to 50° C.
8. The method of claim 2 where the chlorinating agent is selected from the group consisting of phosphoryl chloride, thionyl chloride, phosphorus pentachloride and phosphorus trichloride.
9. The method of claim 5 where the chlorinating agent is thionyl chloride.
10. The method of claim 8 where the reaction is carried out at a temperature above −30° C.
11. The method of claim 9 where the reaction is carried out at temperatures in the range from −10° C. to 50° C.
12. The method of claim 1 where the ratio of moles of component (A) to moles of component (B) is in the range from 1:1 to 1:1.5.
13. The method of claim 10 where the ratio of moles of component (A) to moles of component (B) is in the range from 1:1 to 1:1.5.
14. The method claim 11 where the ratio of moles of component (A) to moles of component (B) is in the range from 1:1 to 1:1.5.
15. The method of claim 1 where components (A) and (B) are reacted neat or in organic solvent.
16. The method of claim 14 where components (A) and (B) are reacted neat or in organic solvent.
17. The fatty acid chloride prepared by the method of claim 1.
18. The fatty acid chloride prepared by the method of claim 5.
19. The fatty acid chloride prepared by the method of claim 9.
20. The fatty acid chloride prepared by the method of claim 14.

* * * * *